(12) United States Patent
Zuo

(10) Patent No.: US 6,939,571 B2
(45) Date of Patent: Sep. 6, 2005

(54) PROCESS OF MAKING AN OSTEOPATHY SOLUTION

(76) Inventor: Xiao-Feng Zuo, Room 602, No. 26, Lane 300, Langao Rode, Shanghai (CN), 200061

( * ) Notice: Subject to any disclaimer, the term of this patent is extended or adjusted under 35 U.S.C. 154(b) by 329 days.

(21) Appl. No.: 10/195,183

(22) Filed: Jul. 16, 2002

(65) Prior Publication Data

US 2004/0013750 A1 Jan. 22, 2004

(51) Int. Cl.$^7$ .................................................. A01N 65/00
(52) U.S. Cl. ...................... 424/748; 424/769; 424/773; 424/774; 424/775; 424/779; 424/725
(58) Field of Search ............................... 424/748, 769, 424/773, 774, 775, 779, 425

*Primary Examiner*—Christopher R. Tate
*Assistant Examiner*—Michele C. Flood
(74) *Attorney, Agent, or Firm*—Raymond Y. Chan; David and Raymond Patent Group

(57) ABSTRACT

A process of making an osteopathy solution includes the steps of (a) soaking a raw composition which includes *Radix Angelicae Sinensis, Radix Paeoniae Rubra, Rhizoma seu Radix Notopterygii, Radix Angelicae Dahuricae, Herba Asari, Folium Artemisiae Argyi, Radix Angelicae Pubescentis, Radix Dipsaci, Myrrha, Ramulus Mori, Radix Rubiae, Radix Clematidis, Radix Stephaniae Tetrandrae, Rhizoma Cimicifugae* and *Radix Gentianae Macrophyllae* in a predetermined amount of water for a predetermined period of soaking time to form a pre-decocting solution and a pre-decocting composition; (b) heating the pre-decocting solution and the pre-decocting composition for a predetermined period of reaction time to form a mixture consisting of a residual composition and a solution; wherein a volume ratio of said solution in step (b) and said water in step (a) is approximately 1:3; and (c) cooling down the solution to a predetermined temperature.

20 Claims, 3 Drawing Sheets

| Chinese Pinyin | Pharmaceutical Name | Name in Chinese |
|---|---|---|
| Dang Gui | *Radix Angelicae Sinensis* | 當歸 |
| Chi Shao | *Radix Paeoniae Rubra* | 赤芍 |
| Qiang Huo | *Rhizoma seu Radix Notopterygii* | 羌活 |
| Bai Zhi | *Radix Angelicae Dahuricae* | 白芷 |
| Xi Xin | *Herba Asari* | 細辛 |
| Ai Ye | *Folium Artemisiae Argyi* | 艾葉 |
| Du Huo | *Radix Angelicae Pubescentis* | 獨活 |
| Chuan Duan | *Radix Dipsaci* | 川斷 |
| Mo Yao | *Myrrha* | 沒藥 |
| Sang Zhi | *Ramulus Mori* | 桑枝 |
| Qian Cao | *Radix Rubiae* | 茜草 |
| Wei Lin Xian | *Radix Clematidis* | 威靈仙 |
| Fang Ji | *Radix Stephaniae Tetrandrae* | 防己 |
| Sheng Ma | *Rhizoma Cimicifugae* | 升麻 |
| Qin Jiao | *Radix Gentianae Macrophyllae* | 秦艽 |

FIGURE 3

PROCESS OF MAKING AN OSTEOPATHY SOLUTION

BACKGROUND OF THE PRESENT INVENTION

1. Field of Invention

The present invention relates to a process of making an osteopathy solution, and more particularly to an osteopathy solution for promoting the process of natural healing activities of human bodies.

2. Background of the Present Invention

Health is a kind of balance of our bodies and the environment. Any forms of imbalance in our bodies will initiate the generation of signals from our bodies. Proper reaction should be done for the signal to restore our bodies to normal. If we neglect the signals from our bodies, we will gradually feel uncomfortable and eventually get sick.

The importance of balance of our bodies can be easily shown in our daily lives. For example, when our bodies suffer from deficiency of water, we will feel thirsty. The sense of feeling thirsty is a signal from our bodies to alert us the necessity of drinking water for restoring the balance of our bodies. Therefore, when we receive the signal of feeling thirsty, we may act by drinking water to restore the osmosis of our bodies to normal. However, if we ignore the signal, the level of deficiency of water will gradually increase and our bodies will become very uncomfortable. Under prolonged situation of suffering water deficiency, we will start to get sick and will eventually die of dehydration.

We can always take remedial steps by ourselves to restore the balance of our bodies. For example, if we have excessive exercises, we will feel very tired or even encounter muscular pain. We have the signal of feeling tired or pain, and then our bodies will act by lowering down the metabolic activities of our bodies. Therefore, we consume less energy in our daily work and decrease the seriousness of our tiredness. Though we still need to have a rest to restore the balance of our bodies, the act of lowering metabolic activities of our bodies is an automatic remedial step by ourselves that helps us to lessen or decrease the level of our tiredness and muscular pain so that the balance of our bodies can be maintained.

However, sometimes our bodies cannot withstand the imbalance and the automatic remedial steps by ourselves are not fast in responsive to our imbalance. Therefore, some external precautious steps are required to speed up our automatic remedial action of our bodies and maintain the balance of our bodies.

For example, one of the common signals arisen from the imbalance of our bodies is muscular pain and discomfort. The pain is a signal from our bodies to alert us to take a rest. However, it is always unrealistic to take a rest for this kind of muscular pain and discomfort. Therefore, instead of ignoring the signal from our bodies that may lead to serious adverse consequence, it is better for us to take some extra care to our bodies for restoring the balance.

Under vigorous exercise, our bodies will automatically switch from aerobic respiration to anaerobic respiration so that sufficient energy can be produced for our emergency use. However, the production of extra amount of energy for our emergency use may lead to the accumulation of lactic acid in our muscles and our muscles may become fatigue and exhausted, which is one of the causes of muscular pain and discomfort. If we don't take enough rest for our bodies to allow a thorough flow of oxygen in our bodies for recovery, our bodies will not be able to recover from this kind of imbalance.

We all have the experience of hitting our bodies and the injured parts get swollen. This is another example of our automatic recovery. The injured parts get swollen because our immune system need to protect ourselves from external attack and our circulatory system need to transport more nutrients and antigens to defense ourselves. Thus, the injured parts get swollen as there is an accumulation of nutrients and antigens in the injured parts of our bodies and such act are in fact a reaction to the external attack to restore the balance of our bodies to normal.

Common methods of soothing muscular pain or discomfort are mediation. Medicine, such as anodyne or aspirin, are commonly used to deactivating our sensitivity to pain. However, the balance of our bodies are not restored to normal under this kind of medication and the curing of muscular pain or discomfort is highly depended on our automatic remediation steps of our bodies.

Herbs have been widely used to restore any imbalance of our bodies. External application of the herbs is especially useful for muscular pain or discomfort and the effect of their use has been highly recognized. Although many different kinds of herbs can be used independently for achieving their functions, the use of single herb is not competent to maintain the balance of our bodies. Therefore, there are always difficulties in making and preparing a suitable composition for our need.

SUMMARY OF THE INVENTION

The main object of the present invention is to provide a process of making an osteopathy solution which is a composition of natural herbs for promoting the process of natural restoring activities of human bodies.

Another object of the present invention is to provide a process of making an osteopathy solution which is a composition of natural herbs for increasing blood flow to the immediate portion of muscular pain or discomfort.

Another object of the present invention is to provide a process of making an osteopathy solution which is a composition of natural herbs for increasing oxygen supply to the immediate portion of muscular pain or discomfort.

Another object for the present invention is to provide a process of making an osteopathy solution which is a composition of natural herbs for decreasing the chance of pathologenic or dermatogenic infection of the immediate portion of muscular pain or discomfort.

In order to accomplish the above objects, the present invention provides a process of making an osteopathy solution having a preferred composition which consists of 10.53% by weight of *Radix Angelicae Sinensis*, 10.53% by weight of *Radix Paeoniae Rubra*, 7.02% by weight of *Rhizoma seu Radix Notopterygii*, 7.02% by weight of *Radix Angelicae Dahuricae*, 7.02% by weight of *Herba Asari*, 8.77% by weight of *Folium Artemisiae Argyi*, 5.26% by weight of *Radix Angelicae Pubescentis*, 7.02% by weight of *Radix Dipsaci*, 5.26% by weight of *Myrrha*, 1.75% by weight of *Ramulus Mori*, 5.26% by weight of *Radix Rubiae*, 5.26% by weight of *Radix Clematidis*, 7.02% by weight of *Radix Stephaniae Tetrandrae*, 5.26% by weight of *Rhizoma Cimicifugae*, and 7.02% by weight of *Radix Gentianae Macrophyllae*.

The process of making an osteopathy solution comprises the steps of:

a. soaking a raw composition which consists of *Radix Angelicae Sinensis, Radix Paeoniae Rubra, Rhizoma seu*

Radix Notopterygii, Radix Angelicae Dahuricae, Herba Asari, Folium Artemisiae Argyi, Radix Angelicae Pubescentis, Radix Dipsaci, Myrrha, Ramulus Mori, Radix Rubiae, Radix Clematidis, Radix Stephaniae Tetrandrae, Rhizoma Cimicifugae and Radix Gentianae Macrophyllae in a predetermined amount of water for a predetermined period of soaking time to form a pre-decocting solution and a pre-decocting composition;

b. heating the pre-decocting solution and the pre-decocting composition for a predetermined period of reaction time to form a mixture consisting of a residual composition and a solution; wherein a volume ratio of the solution in step (b) and the water in step (a) is approximately 1:3; and c. cooling down the solution to a predetermined temperature.

BRIEF DESCRIPTION OF THE DRAWINGS

FIG. 3 is a table of original Chinese names and Chinese pinyin of the herbs used in the composition of the osteopathy solution of the present invention.

DETAILED DESCRIPTION OF THE PREFERRED EMBODIMENT

Figure 1:
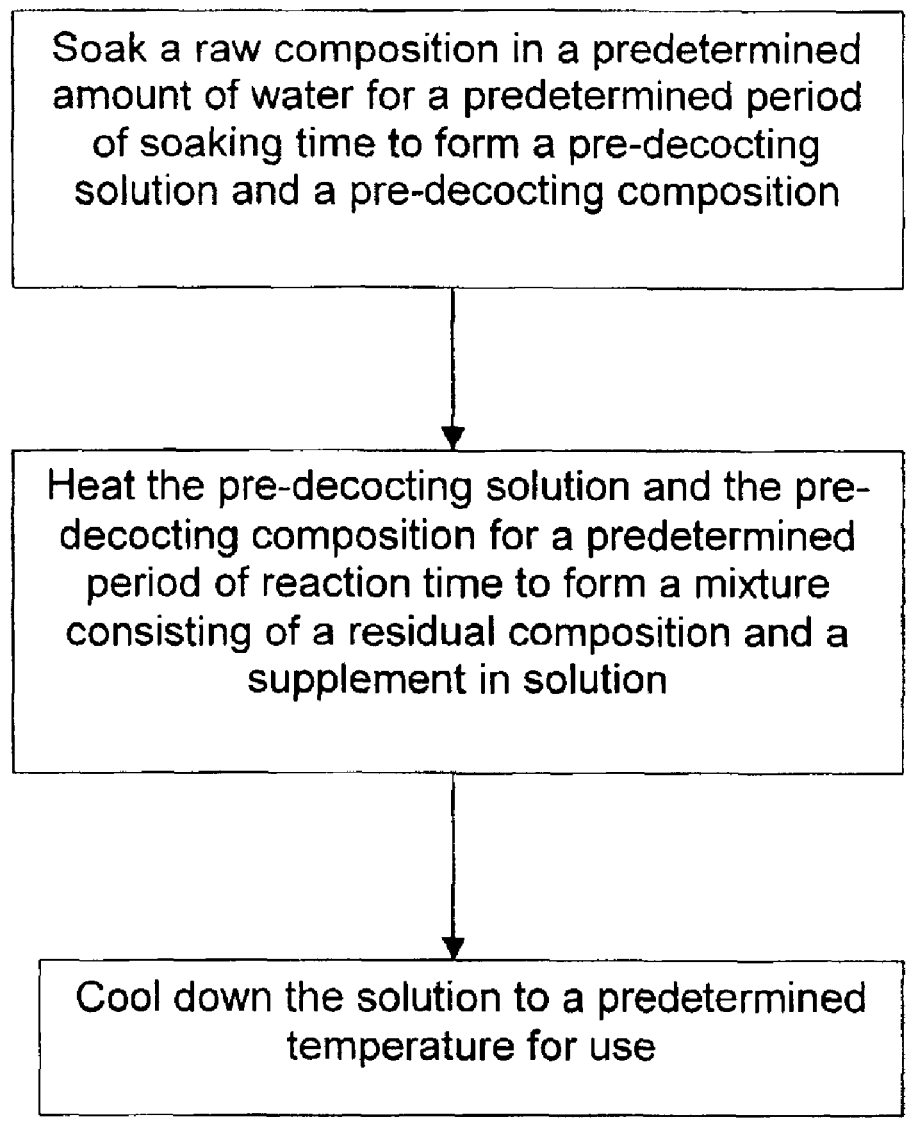
FIG. 1 is a box diagram of a process of making an osteopathy solution.

Referring to FIG. 1, the present invention provides a process of making an osteopathy solution having a preferred composition which includes a 10.53% by weight of *Radix Angelicae Sinensis*, a 10.53% by weight of *Radix Paeoniae Rubra*, a 7.02% by weight of *Rhizoma seu Radix Notopterygii*, a 7.02% by weight of *Radix Angelicae Dahuricae*, a 7.02% by weight of *Herba Asari*, a 8.77% by weight of *Folium Artemisiae Argyi*, a 5.26% by weight of *Radix Angelicae Pubescentis*, a 7.02% by weight of *Radix Dipsaci*, a 5.26% by weight of *Myrrha*, 1.75% by weight of *Ramulus Mori*, a 5.26% by weight of *Radix Rubiae*, a 5.26% by weight of *Radix Clematidis*, a 7.02% by weight of *Radix Stephaniae Tetrandrae*, a 5.26% by weight of *Rhizoma Cimicifugae*, and a 7.02% by weight of *Radix Gentianae Macrophyllae*.

The *Radix Angelicae Sinensis* has been used as Chinese herbal medicine and dietary supplement. Medical research has revealed its significance and beneficiary effects to human bodies. *Radix Angelicae Sinensis* is well known for enriching blood. It has the effect of dilating coronary artery and increasing coronary flow and decreasing oxygen consumption. Thus, it can be used for increasing the blood circulation and increasing the rate of metabolism.

The *Radix Paeoniae Rubra* has been used for clearing away the heat and cooling the blood, and promoting blood circulation to remove blood stasis by having a strong anti-spastic effect with analgesic, sedative, anticonvulsive, anti-bacterial and anti-inflammatory effects; dilating blood vessels, increasing coronary flow and improving myocardial oxygen supply; and inhibit platelets aggregation.

The *Rhizoma seu Radix Notopterygii* has been widely used to expel cold and induce sweating to expel the exogenous evils from the body surface by increasing blood flow to the coronary circulatory system.

The *Radix Angelicae Dahuricae* has been used to expel wind-evil and induce sweating to expel the exogenous evils from the body surface, clear the nasal passage and alleviate pain as well as stimulating the central nervous system of our bodies.

The *Herba Asari* has been widely used to induce sweating to expel cold and exogenous evils from the body surface, expel wind and relieve pain, and warm the lung to promote expectoration.

The *Folium Artemisiae Argyi* has been used to expel cold and alleviate pain, and relieve itching for eczema and dermatitis by inhibiting the growth of various bacteria in vitro and inhibiting the growth of some dermatomyces.

The *Radix Angelicae Pubescentis* has been used to expel wind-dampness, relieve arthralgia, and alleviate pain by its sedative, analgestic and antiphlogistic nature and its Coumarin as antimycotic substance.

The *Radix Dipsaci* has been used to counteracting the deficiency of vitamin E by strengthening the bone and muscle.

The *Myrrha* is the resin form the bark of the *Commiphora myrrha*. It is generally used to removing stasis and promoting blood circulation, and promoting vital energy circulation and relaxing tendons by inhibits the growth of skin fungi and the excessive secretion of bronchi and uterus.

The *Ramulus Mori* is used to expel wind, dredge the channels and ease the joints, lower blood pressure by promoting lymphocyte blastenesis.

The *Radix Rubiae* has been used to cool the blood, promote blood circulation and stop bleeding, remove stasis and relieve pain by is bacteriostatic in vitro natural.

The *Radix Clematidis* has been used to expel wind and dampness, dredge the channel and alleviate pain; disperse lumps and relieve swelling by inhibiting the growth of bacteria.

The *Radix Stephaniae Tetrandrae* has been used to cause diuresis and to relieving rheumatic conditions by edma with oilguria, eczema, rheumatic arthritis, and hypertension.

The *Rhizoma Cimicifugae* has been used to expel wind and hear, clear away toxic materials and let out skin eruption; lift up yang-energy; clear away heat and expel fire by its antipyretic, analgesic and anti-inflammatory natural and inhibiting myocardium, slowing heart rate and lowering blood pressure.

The *Radix Gentiannae Macrophyllae* has been used to clear away heat, expel cold and dampness for arthralgia of wind-dampness-heat type and muscular spasm; lower asthenic fever and promote diuresis, relax the bowels and relieve jaundice by inhibitory effect in arthritis, anti-allergic and inducing transient hypotensive effect.

The present invention provides a process of making an osteopathy solution, as shown in FIG. 1, comprising the steps of:

a. soaking a raw composition which includes a *Radix Angelicae Sinensis*, a *Radix Paeoniae Rubra*, a *Rhizoma seu Radix Notopterygii*, a *Radix Angelicae Dahuricae*, a *Herba Asari*, a *Folium Artemisiae Argyi*, a *Radix Angelicae Pubescentis*, a *Radix Dipsaci*, a *Myrrha*, a *Ramulus Mori*, a *Radix Rubiae*, a *Radix Clematidis*, a *Radix Stephaniae Tetrandrae*, a *Rhizoma Cimicifugae*, and a *Radix Gentianae Macrophyllae* in a predetermined amount of water for a predetermined period of soaking time to form a pre-decocting solution and a pre-decocting composition;

b. heating the pre-decocting solution and the pre-decocting composition for a predetermined period of reaction time to form a mixture consisting of a residual composition and a solution; wherein a volume ratio of the solution in step (b) and the water in step (a) is approximately 1:3; and c. cooling down the solution to a predetermined temperature for use.

The ratio of the weight of the raw composition and the volume of water is approximately 1:6.

When the raw composition of the osteopathy solution is soaked in the predetermined amount of water, the water will be able to penetrate into the raw composition by osmosis and diffusion and soften the raw composition. The preferred soaking time is 30 minutes.

After the predetermined period of soaking time, the pre-decocting solution and the pre-decocting composition will be saturated. Then, heating the pre-decocting composition and the pre-decocting solution will increase the temperature and maintain an optimum environment for reaction activity of the pre-decocting composition and the pre-decocting solution and will shorten the time to reach an equilibrium to form a saturated solution of the osteopathy solution.

Then, the reaction activity is completed and a predetermined volume of solution is obtained. Cooling down the solution to a temperature of 40° before use is preferred. The temperature of 40° is acceptably higher than our body temperature to stimulate circulation and facilitate diffusion when the osteopathy solution is used as a bathing solution or as a massage solution.

The residual composition and the solution can be separated by filtration or sedimentation.

Figure 2:
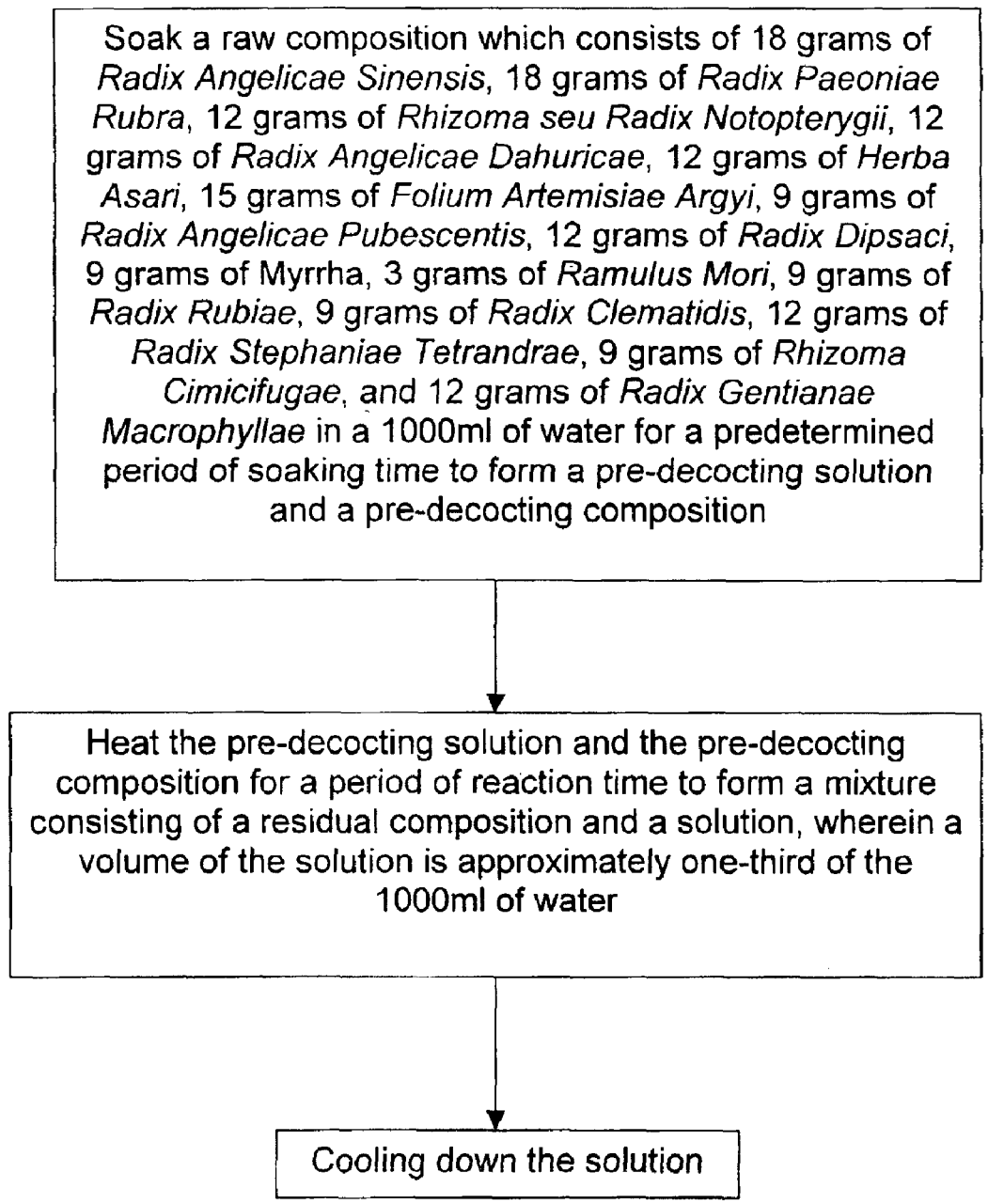
FIG. 2 is a box diagram of a process of making an osteopathy solution of the first preferred embodiment.

Referring to FIG. 2, the present invention provides a process of making an osteopathy solution of the first preferred embodiment, wherein the osteopathy solution has a first preferred composition which consists of 18 grams of *Radix Angelicae Sinensis*, 18 grams of *Radix Paeoniae Rubra*, 12 grams of *Rhizoma seu Radix Notopterygii*, 12 grams of *Radix Angelicae Dahuricae*, 12 grams of *Herba Asari*, 15 grams of *Folium Artemisiae Argyi*, 9 grams of *Radix Angelicae Pubescentis*, 12 grams of *Radix Dipsaci*, 9 grams of *Myrrha*, 3 grams of *Ramulus Mori*, 9 grams of *Radix Rubiae*, 9 grams of *Radix Clematidis*, 12 grams of *Radix Stephaniae Tetrandrae*, 9 grams of *Rhizoma Cimicifugae*, and 12 grams of *Radix Gentianae Macrophyllae*.

The present invention provides a process of making an osteopathy solution of the first preferred embodiment, as shown in FIG. 2, comprising the steps of:

a. soaking the first preferred composition in a 1000 ml of water for a predetermined period of soaking time to form a pre-decocting solution and a pre-decocting composition;

b. heating the pre-decocting solution and the pre-decocting composition for a predetermined period of reaction time to form a mixture consisting of a residual composition and a solution; wherein a volume ratio of the solution in step (b) and the water in step (a) is approximately 1:3; and c. cooling down the solution to a predetermined temperature for use.

When the raw composition of the osteopathy solution is soaked in the predetermined amount of water, the water will be able to penetrate into the raw composition by osmosis and diffusion and soften the raw composition. The preferred soaking time is 30 minutes. After the predetermined period of soaking time, the pre-decocting solution and the pre-decocting composition will be saturated. Then, heating the pre-decocting composition and the pre-decocting solution will increase the temperature and maintain an optimum environment for reaction activity of the pre-decocting composition and the pre-decocting solution and will shorten the time to reach an equilibrium to form a saturated solution of the osteopathy solution. The preferred heating time is 15 minutes. Then, the reaction activity is completed and a predetermined volume of solution is obtained. Cooling down the solution to a temperature of 40° before use is preferred. The temperature of 40° is acceptably higher than our body temperature to stimulate circulation and facilitate diffusion when the osteopathy solution is used as a bathing solution or as a massage solution. The residual composition and the solution can be separated by filtration or sedimentation.

Referring to FIG. 3, the present invention is originated from the use of herbs and the name of the herbs used in the composition for the osteopathy solution is a translation of their Chinese names. The translation is as follows:

| Chinese Pinyin | Pharmaceutical Name | Name in Chinese |
| --- | --- | --- |
| Dang Gui | Radix Angelicae Sinensis | 當歸 |
| Chi Shao | Radix Paeoniae Rubra | 赤芍 |
| Qiang Huo | Rhizoma seu Radix Notopterygii | 羌活 |
| Bai Zhi | Radix Angelicae Dahuricae | 白芷 |
| Xi Xin | Herba Asari | 細辛 |
| Ai Ye | Folium Artemisiae Argyi | 艾葉 |
| Du Huo | Radix Angelicae Pubescentis | 獨活 |
| Chuan Duan | Radix Dipsaci | 川斷 |
| Mo Yao | Myrrha | 沒藥 |
| Sang Zhi | Ramulus Mori | 桑枝 |
| Qian Cao | Radix Rubiae | 茜草 |
| Wei Lin Xian | Radix Clematidis | 威靈仙 |
| Fang Ji | Radix Stephaniae Tetrandrae | 防己 |
| Sheng Ma | Rhizoma Cimicifugae | 升麻 |
| Qin Jiao | Radix Gentianae Macrophyllae | 秦艽 |

What is claimed is:

1. A process of making an osteopathy solution, comprising the steps of:

a. soaking a raw composition which includes a *Radix Angelicae Sinensis*, a *Radix Paeoniae Rubra*, a *Rhizoma seu Radix Notopterygii*, a *Radix Angelicae Dahuricae*, a *Herba Asari*, a *Folium Artemisiae Argyi*, a *Radix Angelicae Pubescentis*, a *Radix Dipsaci*, a *Myrrha*, a *Ramulus Mori*, a *Radix Rubiae*, *Radix Clematidis*, a *Radix Stephaniae Tetrandrae*, a *Rhizoma Cimicifugae*, and a *Radix Gentianae Macrophyllae* in a predetermined amount of water for a predetermined period of soaking time to form a pre-decocting solution and a pre-decocting composition; and b. heating said pre-decocting solution and said pre-decocting composition for a predetermined period of reaction time to form a mixture consisting of a residual composition and a solution; wherein a volume ratio of said solution in step (b) and said water in step (a) is approximately 1:3.

2. The process, as recited in claim 1, wherein said raw composition includes 10.53% by weight of said *Radix Angelicae Sinensis*, 10.53% by weight of said *Radix Paeoniae Rubra*, 7.02% by weight of said *Rhizoma seu Radix Notopterygii*, 7.02% by weight of said *Radix Angelicae Dahuricae*, 7.02% by weight of said *Herba Asari*, 8.77% by weight of said *Folium Artemisiae Argyi*, 5.26% by weight of said *Radix Angelicae Pubescentis*, 7.02% by weight of said *Radix Dipsaci*, 5.26% by weight of said *Myrrha*, 1.75% by weight of said *Ramulus Mori*, 5.26% by weight of said *Radix Rubiae*, 5.26% by weight of said *Radix Clematidis*, 7.02% by weight of said *Radix Stephaniae Tetrandrae*, 5.26% by weight of said *Rhizoma Cimicifugae*, and 7.02% by weight of said *Radix Gentianae Macrophyllae*.

3. The process, as recited in claim 1, wherein said raw composition includes 18 grams of said *Radix Angelicae Sinensis*, 18 grams of said *Radix Paeoniae Rubra*, 12 grams of said *Rhizoma seu Radix Notopterygii*, 12 grams of said *Radix Angelicae Dahuricae*, 12 grams of said *Herba Asari*, 15 grams of said *Folium Artemisiae Argyi*, 9 grams of said *Radix Angelicae Pubescentis*, 12 grams of said *Radix Dipsaci*, 9 grams of said *Myrrha*, 3 grams of said *Ramulus Mori*, 9 grams of said *Radix Rubiae*, 9 grams of said *Radix Clematidis*, 12 grams of said *Radix Stephaniae Tetrandrae*, 9 grams of said *Rhizoma Cimicifugae*, and 12 grams of said *Radix Gentianae Macrophyllae*, wherein said raw composition is soaked in a 1000 ml of said water.

4. The process, as recited in claim 2, further comprising a step of separating said residual composition and said solution.

5. The process, as recited in claim 3, further comprising a step of separating said residual composition and said solution.

6. The process, as recited in claim 4, further comprising a step of cooling said solution to room temperature.

7. The process, as recited in claim 5, further comprising a step of cooling said solution to room temperature.

8. The process, as recited in claim 4, wherein said soaking time is 30 minutes.

9. The process, as recited in claim 5, wherein said soaking time is 30 minutes.

10. The process, as recited in claim 6, wherein said soaking time is 30 minutes.

11. The process, as recited in claim 4, wherein a ratio of said water in ml and said raw composition in grams is 6:1.

12. The process, as recited in claim 5, wherein a ratio of said water in ml and said raw composition in grams is 6:1.

13. The process, as recited in claim 10, wherein a ratio of said water in ml and said raw composition in grams is 6:1.

14. An osteopathy solution produced by a process which comprises the steps of:
   a. soaking a raw composition which includes a *Radix Angelicae Sinensis*, a *Radix Paeoniae Rubra*, a *Rhizoma seu Radix Notopterygii*, a *Radix Angelicae Dahuricae*, a *Herba Asari*, a *Folium Artemisiae Argyi*, a *Radix Angelicae Pubescentis*, a *Radix Dipsaci*, a *Myrrha*, a *Ramulus Mori*, a *Radix Rubiae, Radix Clematidis*, a *Radix Stephaniae Tetrandrae*, a *Rhizoma Cimicifugae*, and a *Radix Gentianae Macrophyllae* in a predetermined amount of water for a predetermined period of soaking time to form a pre-decocting solution and a pre-decocting composition; and
   b. heating said pre-decocting solution and said pre-decocting composition for a predetermined period of reaction time to form a mixture consisting of a residual composition and a solution; wherein a volume ratio of said solution in step (b) and said water in step (a) is approximately 1:3.

15. The osteopathy solution, as recited in claim 14, wherein said raw composition includes 10.53% by weight of said *Radix Angelicae Sinensis*, 10.53% by weight of said *Radix Paeoniae Rubra*, 7.02% by weight of said *Rhizoma seu Radix Notopterygii*, 7.02% by weight of said *Radix Angelicae Dahuricae*, 7.02% by weight of said *Herba Asari*, 8.77% by weight of said *Folium Artemisiae Argyi*, 5.26% by weight of said *Radix Angelicae Pubescentis*, 7.02% by weight of said *Radix Dipsaci*, 5.26% by weight of said *Myrrha*, 1.75% by weight of said *Ramulus Mori*, 5.26% by weight of said *Radix Rubiae*, 5.26% by weight of said *Radix Clematidis*, 7.02% by weight of said *Radix Stephaniae Tetrandrae*, 5.26% by weight of said *Rhizoma Cimicifugae*, and 7.02% by weight of said *Radix Gentianae Macrophyllae*.

16. The osteopathy solution, as recited in claim 14, wherein said raw composition includes 18 grams of said *Radix Angelicae Sinensis*, 18 grams of said *Radix Paeoniae Rubra*, 12 grams of said *Rhizoma seu Radix Notopterygii*, 12 grams of said *Radix Angelicae Dahuricae*, 12 grams of said *Herba Asari*, 15 grams of said *Folium Artemisiae Argyi*, 9 grams of said *Radix Angelicae Pubescentis*, 12 grams of said *Radix Dipsaci*, 9 grams of said *Myrrha*, 3 grams of said *Ramulus Mori*, 9 grams of said *Radix Rubiae*, 9 grams of said *Radix Clematidis*, 12 grams of said *Radix Stephaniae Tetrandrae*, 9 grams of said *Rhizoma Cimicifugae, and* 12 grams of said *Radix Gentianae Macrophyllae*, wherein said raw composition is soaked in a 1000 ml of said water.

17. The osteopathy solution, as recited in claim 15, further comprising a step of separating said residual composition and said solution.

18. The osteopathy solution, as recited in claim 16, further comprising a step of separating said residual composition and said solution.

19. The osteopathy solution, as recited in claim 17, further comprising a step of cooling said solution to a room temperature, wherein said soaking time is 30 minutes and a ratio of said water in ml and said raw composition in grams is 6:1.

20. The osteopathy solution, as recited in claim 18, further comprising a step of cooling said solution to a room temperature, wherein said soaking time is 30 minutes and a ratio of said water in ml and said raw composition in grams is 6:1.

* * * * *